(12) United States Patent
Takada

(10) Patent No.: US 6,607,891 B1
(45) Date of Patent: Aug. 19, 2003

(54) METHOD OF ASSAYING INSULIN-LIKE GROWTH FACTOR

(75) Inventor: Makoto Takada, Ibaraki (JP)

(73) Assignee: Mitsubishi Chemical Corporation, Tokyo (JP)

(*) Notice: Subject to any disclaimer, the term of this patent is extended or adjusted under 35 U.S.C. 154(b) by 0 days.

(21) Appl. No.: 09/744,255

(22) PCT Filed: Jul. 30, 1999

(86) PCT No.: PCT/JP99/04112

§ 371 (c)(1),
(2), (4) Date: Jan. 31, 2001

(87) PCT Pub. No.: WO00/07021

PCT Pub. Date: Feb. 10, 2000

(30) Foreign Application Priority Data

Jul. 31, 1998 (JP) .......................................... 10-217864
Dec. 24, 1998 (JP) .......................................... 10-366568

(51) Int. Cl.$^7$ ...................... G01N 33/53; G01N 33/543; G01N 33/546; G01N 33/553
(52) U.S. Cl. ...................... 435/7.1; 435/7.92; 435/7.93; 435/7.94; 435/7.95; 435/961; 435/962; 436/518; 436/523; 436/526; 436/528; 436/534; 436/543; 436/174; 436/175; 436/177; 436/825
(58) Field of Search ................................ 435/7.1, 7.92, 435/7.93, 7.94, 7.95, 810, 961, 962, 975; 436/518, 523, 526, 528, 534, 172, 174, 175, 177, 817, 825, 543

(56) References Cited

U.S. PATENT DOCUMENTS

| | | |
|---|---|---|
| 4,111,657 A | 9/1978 | Denney et al. |
| 4,950,612 A | 8/1990 | Khanna et al. |
| 5,135,875 A | 8/1992 | Meucci et al. |
| 5,332,678 A | 7/1994 | Hoyle |
| 5,691,150 A | 11/1997 | Mori et al. |
| 5,851,907 A * | 12/1998 | Mohan et al. ............... 436/518 |

FOREIGN PATENT DOCUMENTS

| | | |
|---|---|---|
| EP | 0 492 552 | 7/1992 |
| EP | 0 713 096 A1 | 5/1996 |
| JP | 53-093097 | 8/1978 |
| JP | 4-233460 | 8/1992 |
| JP | 5-252987 | 10/1993 |
| JP | 6-102275 | 4/1994 |
| JP | 7-509783 | 10/1995 |
| JP | 8-145998 | 6/1996 |
| JP | 8-166382 | 6/1996 |
| JP | 8-178921 | 7/1996 |
| WO | WO 94/10571 | 5/1994 |

OTHER PUBLICATIONS

Khosravi et al., 1997. Immunoassay of acid–labile subunit of human insulin–like growth factor binding complex in serum. Clinical Chemistry 43 (6 Part 2): S170, Abstract #290.*
Mason et al., *Ann Clin Biochem*, vol. 33, pp. 201–208, 1996.
Boge et al., *Analytical Biochemistry*, vol. 216, pp. 406–412, 1994.
Laemmli, *Nature*, vol. 227, pp. 680–685, 1970.
W.H. Daughaday, et al., Journal of Clinical Endocrinology and Metabolism, vol. 51, No. 4, pps. 781–788, "Inhibition of Access of Bound Somatomedin to Membrane Receptor and Immunobinding Sites: A Comparison of Radioreceptor and Radioimmunoassay of Somtomedin in Native and Acid–Ethanol–Extracted Serum," 1980.
W.F. Blum, et al., Acta Endocrinologica, vol. 118, pps. 374–380, "A Specific Radioimmunoassay for Insulin–Like Growth Factor II: The Interference of IGF Binding Proteins Can be Blocked by Excess IFG–I," 1988.

* cited by examiner

Primary Examiner—Christopher L. Chin
Assistant Examiner—James L. Grun
(74) Attorney, Agent, or Firm—Oblon, Spivak, McClelland, Maier & Neustadt, P.C.

(57) ABSTRACT

A pretreatment method for assaying a substance which comprises mixing a biological specimen with at least one pretreating agent selected from among surfactants and alkali agents, thus releasing binding proteins in the biological specimen from the substance to be assayed and, at the same time, inactivating the proteins by irreversible denaturation to thereby eliminate the effects of the binding proteins coexisting in the biological specimen.

11 Claims, 1 Drawing Sheet

TOTAL RADIOACTIVITY: 211717 cpm
NSB: 233 cpm

TOTAL RADIOACTIVITY: 193207 cpm
NSB: 270 cpm

METHOD OF ASSAYING INSULIN-LIKE GROWTH FACTOR

TECHNICAL FIELD

This invention relates to a method of assaying a bioactive component in a biological specimen by an assay with the use of an antibody, a binding protein or a receptor.

BACKGROUND ART

Many bioactive components such as growth factors, hormones, vitamins and medicaments are bound to binding proteins so that the effects and metabolic speeds thereof are controlled in vivo. In case of assaying bioactive components by assay with the use of antibodies, binding proteins or receptors, these coexisting binding proteins frequently affect the assay data.

In case where a substance to be assayed coexists with binding proteins in a biological specimen, it has been a practice to carry out various pretreatment to eliminate the effects of the binding proteins on the assay. In the case of insulin-like growth factor 1 (IGF-I), for example, the "acid-ethanol method" may be cited as the method which is most commonly employed at present (W. H. Daughaday, *Journal of Clinical Endocrinology and Metabolism*, 1980, Vol. 51, p. 781–788). This method utilizes a phenomenon that when a biological specimen is treated with a mixture of hydrochloric acid with ethanol, binding proteins releasing IGF-I under acidic conditions become insoluble in the ethanol atmosphere and thus can be easily eliminated from the specimen by centrifugation.

In the case where centrifugation is omitted in the acid-ethanol method, however, the binding activity of the binding proteins to IGF-I is restored at the point of neutralization and thus affects the assay data. To overcome this problem, JP-A-8-145998 reports a method wherein a re-binding inhibitor is added to a neutralizing buffer to be used after the acid treatment (the term "JP-A" as used herein means an "unexamined published Japanese patent application"). Since it is considered that IGF-I all exists in the free form in the neutralized biological specimen solution in this method, the assay data are not affected by the coexisting binding proteins. As the re-binding inhibitor, use is made of 8-anilino-1-naphthalenesulfonic acid salt (ANS) and the like.

ANS, which has been used for a long time to release thyroid hormone from binding proteins, suffers from some problems such as being unstable to light and atmospheric oxidation and having a strong toxicity. In addition, it is pointed out that ANS sometimes affects immuno reactions, which restricts the utilization of ANS in assaying biological specimens.

As methods for eliminating the effects of binding proteins contained in specimens, Japanese Patent No. 1,940,596 proposes a method wherein, in analyzing vitamin $B_{12}$, thiol group is introduced into binding proteins so as to inactivate the binding activity to vitamin $B_{12}$ while Japanese Patent No. 2,023,927 proposes a method wherein binding proteins are denatured by using a peroxy acid. However, denaturing agents should be added in excess in these known methods and it is therefore needed to inactivate the excessive denaturing agents after the completion of the denaturation of the binding proteins.

There is known a method of assaying IGF-I by adding IGF-II in excess to a specimen. Since IGF-II blocks all of the binding sites of binding proteins, IGF-I, which has been thus driven away and released, is immunologically assayed in this method (W. F. Blum, Acta Endocrinokogica, 1988, Vol. 118, p.374–380). In this method, it is necessary to use antibodies which would not have crossreactivity with IGF-II. Since IGF-I is closely similar in structure to IGF-II, it is highly difficult to obtain antibodies which are never affected by IGF-II added in excess in the pretreatment. Although JP-A-6-102275 reports a similar method for assaying a steroid hormone, this method suffers from some problems such that an assay system usable therefor is restricted and costs a great deal.

To eliminate the effects of binding proteins coexisting in biological specimens, it is needed in the conventional art to add expensive reagents or highly toxic reagents to pretreating agents, neutralizing agents or assay buffers or to employ troublesome procedures or special instruments, as described above. Therefore, it has been required to solve these problems encountering in the existing methods.

DISCLOSURE OF THE INVENTION

It has been found out in the invention that when a specific pretreating agent is added to a specimen at such a level as not affecting the activity of the substance to be assayed, binding proteins are exclusively inactivated and the thus obtained mixture can be subjected to the assay as such.

That is to say, by exposing a biological specimen to a surfactant and/or an alkali agent, the binding proteins are released from a substance to be assayed and irreversibly denatured simultaneously. The thus pretreated specimen may be neutralized or diluted so that the pH value attains a level appropriate for the assay, while requiring neither neutralization of a functional group of a denaturing agent nor addition of any special material preventing the substance to be assayed from re-binding to the binding proteins. Alternatively, the pretreated specimen may be subjected to the assay as such.

BEST MODE FOR CARRYING OUT THE INVENTION

Figure 1:
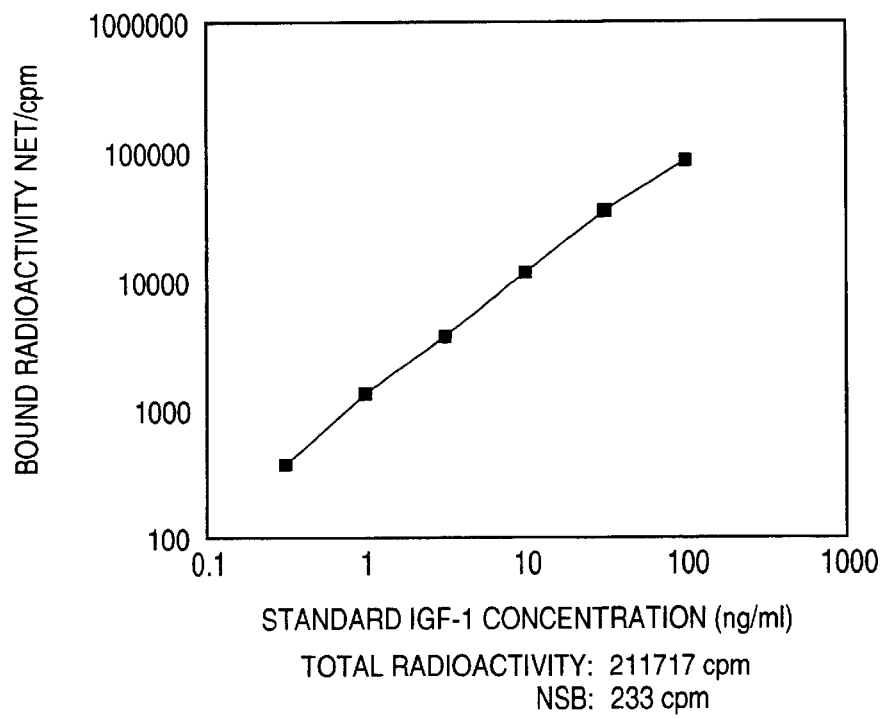
FIG. 1 shows a calibration curve of the bound radioactivity of the IGF-I standards obtained in Example 1.

The term "binding proteins" as used in the invention means any proteins capable of binding to the bioactive component to be assayed without restriction. Examples of the binding proteins include insulin-like growth factor-binding proteins, growth hormone-binding proteins, insulin antibodies and thyroid hormone-binding proteins.

The invention provides an assay system whereby growth factors (in particular, insulin-like growth factor 1 and insulin-like growth factor 2), hormones, vitamins, medicaments, amino acids, amino acid metabolites, peptides or proteins contained in biological specimens typified by body fluids such as serum, plasma or urine can be pretreated without worsening the accuracy of the assay system and without resort to any troublesome procedures or special and highly dangerous reagents.

In the invention, a surfactant and/or an alkali agent are used as a pretreating agent. The pretreating agent is usually employed as an aqueous medium. In case of using two or more components, these components may be employed either as separate liquors or as a mixture, though the latter is preferable in practice.

As the surfactant, use can be made of an anionic surfactant, a cationic surfactant, a nonionic surfactant or an amphoteric surfactant. It is preferable to use an anionic surfactant.

Examples of the anionic surfactant include alkylbenzenesulfonates and sodium dodecyl sulfate (hereinafter referred to simply as SDS). Examples of the cationic surfactant include dodecyltrimethylammonium chloride and didodecyldimethylammonium chloride. Examples of the nonionic surfactant include alkylpolyoxyethylene ethers, alkylpolyoxyethylene phenols and polyoxyethylene sorbitan alkyl esters (Tween). Examples of the amphoteric surfactant include alkyltrimethylammonium salts.

In the invention, it is preferable to use an anionic surfactant, still preferably SDS.

The concentration of the surfactant in the pretreating agent ranges, for example, from 0.01 to 5% by weight, preferably from 0.05 to 1% by weight, though it is favorable to determine the optimum concentration depending on the subject to be assayed and the surfactant employed.

On the other hand, examples of the alkali agent include sodium hydroxide, potassium hydroxide and ammonia. Sodium hydroxide is particularly preferable. The concentration of the alkali agent in the pretreating agent usually ranges from 0.001 to 1% by weight.

The pretreating agent may further contain various components (a denaturing agent, a releasing agent, etc.), for example, a lower aliphatic alcohol. Examples of this alcohol include methanol, ethanol, isopropanol and butanol. Among all, ethanol is the most favorable one. It is desirable that the alcohol is employed in an amount of 25 to 35% by weight based on the whole pretreating agent.

As described above, the effects of binding proteins in a biological specimen can be controlled by mixing the pretreating agent with the biological specimen. In this pretreatment, a sufficient effect can be established by stirring usually at around room temperature (for example, from 10 to 40° C.).

In this mixing treatment, the surfactant is supplied to the biological specimen in an amount of usually from 0.01 to 5% by weight, preferably from 0.05 to 1% by weight, on the basis of the biological specimen. On the other hand, the alkali agent is supplied to the biological specimen in an amount of usually from 0.001 to 1% by weight, preferably from 0.01 to 0.5% by weight on the basis of the biological specimen. The amount of such an alkali agent may be appropriately controlled; that is to say, it may be used in a smaller amount in case of using together with the surfactant, and in case of using alone, it may be used in a larger amount.

In the invention, the undesirable effect of the binding proteins in the biological specimen can be eliminated by the above-described pretreatment. Subsequently, the liquid mixture is subjected to the assay of the bioactive component by using a publicly known assay method. The assay method is not particularly restricted, so long as the bioactive component to be assayed can be assayed thereby. Examples of the assay method include the competition method and the sandwich method. In the method of the invention, the above-described liquid mixture is not subjected to some special procedures (solid/liquid separation, extraction, etc.) but employed in the assay as such.

In the competitive assay method or the sandwich method, use can be made of an antibody, a binding protein or a receptors. Examples of these methods include an immunoassay method with the use of a radioactive substance, an enzyme, a fluorescent substance or a chemical luminescent substrate as a label; and an agglutination assay method with the use of a latex, a magnetic latex or a fluorescence labeled latex.

The invention further involves assay kits. Examples of reagents constituting these kits include at least the following components. For example, a kit for assaying insulin-like growth factor (IGF) contains: in case of the sandwich method, e.g.:
 (a) a pretreating liquid containing a surfactant;
 (b) a labeled anti-IGF antibody; and
 (c) a solid phase anti-IGF antibody;
in case of the competition method, e.g.:
 (a) a pretreating liquid containing a surfactant;
 (b) a labeled IGF; and
 (c) an anti-IGF antibody;
in case of the agglutination method with the use of a latex, e.g.;
 (a) a pretreating liquid containing a surfactant;
 (b) a latex having IGF fixed thereto; and
 (c) an anti-IGF antibody; and
in case the sandwich method with the use of a fluorescence labeled latex, e.g.:
 (a) a pretreating liquid containing a surfactant;
 (b) a fluorescence (europium) labeled latex having an anti-IGF antibody fixed thereto; and
 (c) a magnetic latex having an anti-IGF antibody fixed thereto.

Now, the invention will be described by reference to the following Examples. However, it is to be understood that the invention is not construed as being restricted thereto.

EXAMPLE 1

(Assay of Insulin-like Growth Factor 1 (IGF-I) by Using Surfactant)

a) Preparation of Pretreating Liquor
 (1) 0.15% SDS was prepared.
 (2) An acid-ethanol solution for comparison containing 0.1 M of HCl and 90% of ethanol was prepared to give a pretreating liquor.

b) Preparation of Antibody Beads

An anti-IGF-I monoclonal antibody was adsorbed on polystyrene beads under alkaline conditions and subjected to the assay.

c) Preparation of Tracer

Iodine$^{125}$ was introduced by the chloramine T method into a monoclonal antibody capable of forming a sandwich against IGF-I together with the antibody as described in the above b). The thus obtained tracer was diluted with the phosphate buffer as specified below containing bovine serum albumin, etc. and subjected to the assay:
 0.1 M sodium phosphate buffer (pH 7.4);
 0.15 M of sodium chloride;
 10 mM of disodium edetate;
 0.1% of bovine serum albumin;
 0.1% of Tween 20 (surfactant); and
 0.02% of sodium azide.

d) Preparation of IGF-I Standards

IGF-I obtained from Toyobo Co., Ltd. was diluted with the same phosphate buffer containing bovine serum albumin, etc. as described above to give concentrations of 0.3 to 100 ng/ml.

e) Acquisition of Human Serum Specimens

Blood specimens were collected from healthy subjects. After separating, the serum specimens were quickly frozen and stored until using.

f) Pretreatment of Specimens

25 μl of a human serum specimen was taken into a test tube and 500 μl of the pretreating liquor described in the above (1) or (2) was added thereto. In case of the pretreating liquor of the above (1), the specimen was stirred and then immediately subjected to the assay. In case of the acid-ethanol extract of the above (2), the specimen was stirred and then centrifuged and the supernatant was subjected to the assay.

g) Immunoassay

25 μl portions of the IGF-I standards and the pretreated specimens were respectively taken into test tubes and 300 μl of the tracer solution was added to each. After mixing, one antibody bead was put into each test tube. After stirring at room temperature for 2 hours, the bead was washed with 3 ml portions of purified water twice. Then the radioactivity bound to the antibody bead was measured with a γ-counter. A calibration curve was formed based on the bound radioactivity levels of IGF-I standards of 7 concentrations (Table 1 and FIG. 1).

TABLE 1

| Concentration of standard solution (ng/ml) | Bound radioactivity level (B) (cpm) | B/T (%) | Coefficient of variation (%) |
|---|---|---|---|
| 0 (NSB) | 236 | 0.1 | 0.6 |
| 0.3 | 299 | 0.2 | 7.7 |
| 1 | 1190 | 0.7 | 0.2 |
| 3 | 3209 | 1.8 | 1.8 |
| 10 | 10425 | 5.7 | 3.8 |
| 30 | 31432 | 17.2 | 2.0 |
| 100 | 79172 | 43.4 | 0.0 |

Total Radioactivity (T): 182539 cpm.

In case of each standard other than NSB, the bound radioactivity level (B) is expressed in the value calculated by subtracting the bound radioactivity level of NSB (236 cpm).

The IGF-I concentration in each pretreated specimen was determined from the standard curve and the bound radioactivity level of the pretreated specimen, and the IGF-I concentration in the untreated specimen was determined by multiplying the concentration of the pretreated specimen by 21. Table 2 shows the results.

TABLE 2

| Specimen No. | (2) 0.1 M HCl + 90% ethanol (ng/ml) | (1) 0.15% SDS (ng/ml) | (1)/(2) (%) |
|---|---|---|---|
| 1 | 177 | 172 | 97 |
| 2 | 167 | 172 | 103 |
| 3 | 453 | 450 | 99 |
| 4 | 540 | 512 | 95 |
| 5 | 230 | 281 | 100 |

EXAMPLE 2

(Assay of Insulin-like Growth Factor 1 (IGF-I) by Using Surfactant)

As in Example 1, the IGF-I concentrations in specimens were measured and compared by using, as pretreating liquors, (1) a mixture of 0.1 M HCl with 90% ethanol and (2) a mixture of 0.18% SDS, 1 mM NaOH and 30% ethanol. Table 3 shows the results.

TABLE 3

| Specimen No. | (1) 0.1 M HCl + 90% ethanol (ng/ml) | (2) 1 mM NaOH + 0.18% SDS + 30% ethanol (ng/ml) | (2)/(1) (%) |
|---|---|---|---|
| 1 | 177 | 184 | 104 |
| 2 | 167 | 179 | 107 |
| 3 | 453 | 460 | 102 |
| 4 | 540 | 541 | 100 |
| 5 | 230 | 229 | 100 |

Compared with the (1) (0.1 M HCl+90% ethanol), the (2) 1 mM NaOH+0.18% SDS+30% ethanol) could improve the performance.

EXAMPLE 3

(Assay of Insulin-like Growth Factor 1 (IGF-I) by Using Alkali Agent)

a) Preparation of Pretreating Liquor (1) A 50 mM aqueous solution of sodium hydroxide was prepared.

(2) An acid-ethanol solution for control was prepared by adding 9 parts by volume of ethanol to 1 part by volume of 1 N hydrochloric acid to give a pretreating liquor.

Figure 2:
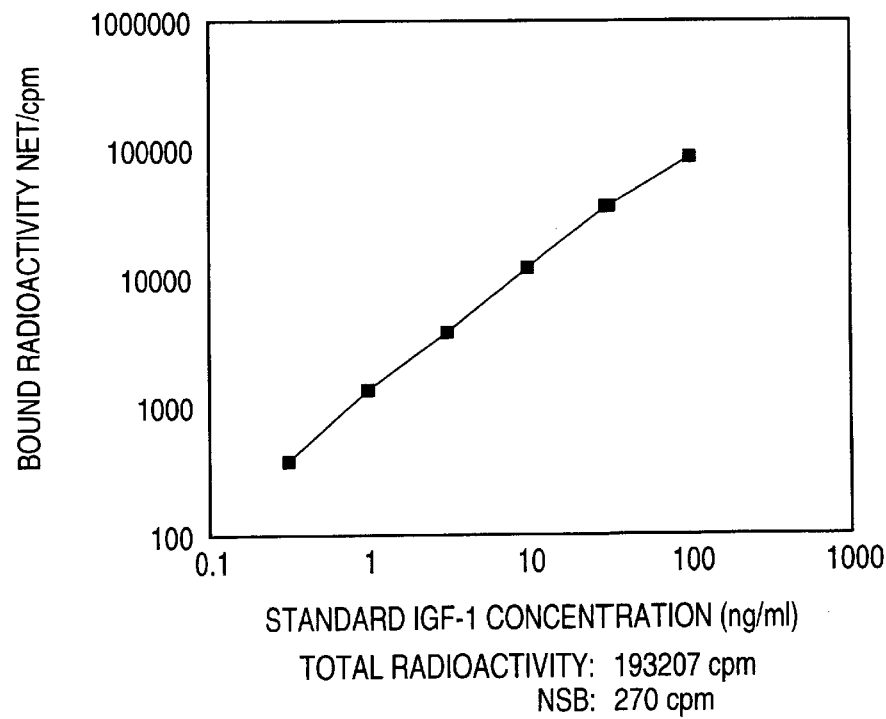
FIG. 2 shows a calibration curve of the bound radioactivity of the IGF-I standards obtained in Example 3.

Subsequently, b) preparation of antibody beads, c) preparation of tracer, d) preparation of IGF-I standards, e) acquisition of human serum specimens and f) pretreatment of specimens were carried out respectively as in Example 1. g) Immunoassay 25 μl portions of the IGF-I standards and the pretreated specimens were respectively taken into test tubes and 300 μl of the tracer solution was added to each. After mixing, one antibody bead was put into each test tube. After stirring at room temperature for 2 hours, the bead was washed with 3 ml portions of purified water twice. Then the radioactivity bound to the antibody bead was measured with a γ-counter. A calibration curve was formed based on the bound radioactivity levels of IGF-I standards of 7 concentrations (Table 4 and FIG. 2).

TABLE 4

| Concentration of standard solution (ng/ml) | Bound radioactivity level (B) (cpm) | B/T (%) | Coefficient of variation (%) |
|---|---|---|---|
| 0 (NSB) | 270 | 0.1 | 3.6 |
| 0.3 | 343 | 0.2 | 8.4 |
| 1 | 1214 | 0.6 | 2.2 |
| 3 | 3454 | 1.8 | 0.3 |
| 10 | 10859 | 5.6 | 2.2 |
| 30 | 33023 | 17.1 | 2.0 |
| 100 | 82917 | 42.9 | 0.0 |

Total radioativity (T): 193207 cpm.

In case of each standard other than NSB, the bound radioactivity level (B) is expressed in the value calculated by subtracting the bound radioactivity level of NSB (270 cpm).

The IGF-I concentration in each pretreated specimen was determined from the standard curve and the bound radioactivity level of the pretreated specimen, and the IGF-I concentration in the untreated specimen was determined by multiplying the concentration of the pretreated specimen by 21. Table 5 shows the results.

TABLE 5

| Specimen No. | (2) 0.1 M HCl + 90% ethanol (ng/ml) | (1) 50 mM NaOH method (ng/ml) | (1)/(2) (%) |
|---|---|---|---|
| 1 | 90 | 87 | 97 |
| 2 | 141 | 151 | 107 |
| 3 | 187 | 179 | 96 |
| 4 | 266 | 279 | 105 |
| 5 | 547 | 574 | 105 |

EXAMPLE 4

(Assay of Insulin-like Growth Factor 1 (IGF-I) by Using Alkali Agent and Ethanol)

As in Example 3, the IGF-I concentrations in specimens were measured and compared by using, as pretreating liquors, (2) a 50 mM NaOH solution alone and (3) a mixture of 5 mM NaOH with 30% ethanol, and as a control, (1) a mixture of 0.1 M HCl with 90% ethanol. Table 6 shows the results.

TABLE 6

| Specimen No. | (1) 0.1 M HCL + 90% ethanol (ng/ml) | (2) 50 mM NaOH (ng/ml) ((2)/(1)%) | (3) 50 mM NaOH + 30% ethanol (ng/ml) (3)/(1)%) |
|---|---|---|---|
| 1 | 266 | 279 (104.9) | 242 (91.0) |
| 2 | 547 | 574 (104.9) | 528 (96.5) |
| 3 | 187 | 179 (95.7) | 197 (105.4) |
| 4 | 141 | 151 (107.1) | 142 (100.7) |
| 5 | 90 | 87 (96.7) | 91 (101.1) |

Compared with the case of using 50 mM NaOH alone, the NaOH concentration was lowered to 5 mM in the case of the combined use. Thus, the storage stability of the specimens after the pretreatment can be improved and the risk of the exposure of workers to an alkali solution of a high concentration can be relieved.

Industrial Applicability

According to the invention, a surfactant is employed in the pretreatment at such a concentration that coexisting binding proteins are exclusively inactivated without damaging the activity of a substance to be assayed. Thus, the concentration of the substance be assayed in a biological specimen can be accurately determined without resort to any expensive reagents, highly toxic reagents, troublesome procedures or special instruments.

What is claimed is:

1. A method of assaying an insulin-like growth factor (IGF), consisting essentially of:
   (i) adding at least one pretreating agent selected from the group consisting of an anionic surfactant and an alkali agent to a biological sample, at such a level to not negatively affect any activity of any IGF in said biological sample in an IGF determination assay and to dissociate any complex of IGF and IGF binding protein in said biological sample and to inactivate any IGF binding protein in said biological sample, to obtain a mixture of said biological sample and said pretreating agent; and
   (ii) subjecting said mixture of said biological sample and said pretreating agent to an assay for IGF presence or amount.

2. The method of claim 1, wherein said pretreating agent is an anionic surfactant and said anionic surfactant is sodium dodecyl sulfate (SDS).

3. The method of claim 1, wherein said pretreating agent is an alkali agent and said alkali agent is sodium hydroxide, potassium hydroxide, or aqueous ammonia.

4. The method of claim 1, wherein said surfactant is present in said pretreating agent in a concentration of 0.01 to 5% by weight.

5. The method of claim 1, wherein said alkali agent is present in said pretreating agent in a concentration of 0.001 to 1% by weight.

6. The method of claim 1, wherein both said anionic surfactant and alkali pretreating agents are added in a single pretreating composition.

7. The method of claim 1, wherein a lower aliphatic alcohol is added in combination with said at least one pretreating agent in a single pretreating composition.

8. The method of claim 7, wherein said lower aliphatic alcohol is ethanol.

9. The method of claim 7, wherein said lower aliphatic alcohol is present in said pretreating composition in a concentration of 25 to 35% by weight.

10. The method of claim 7, wherein said biological specimen is body fluid.

11. The method of claim 1, wherein said assay for IGF comprises the following steps:
    (i) adding an anti-IGF antibody to said mixture, and
    (ii) detecting a complex of IGF and said anti-IGF antibody, as an indication of the presence or amount of IGF in said biological sample.

* * * * *